(12) United States Patent
Beaumont

(10) Patent No.: US 10,799,314 B2
(45) Date of Patent: Oct. 13, 2020

(54) ELECTRONIC VISION SYSTEM AND USE THEREOF

(71) Applicant: DECTRONIQUE (1984) INC., Québec (CA)

(72) Inventor: Clément Beaumont, Beauport (CA)

(73) Assignee: DECTRONIQUE (1984) INC., Québec (CA)

( * ) Notice: Subject to any disclaimer, the term of this patent is extended or adjusted under 35 U.S.C. 154(b) by 49 days.

(21) Appl. No.: 15/762,129

(22) PCT Filed: Sep. 22, 2016

(86) PCT No.: PCT/CA2016/051104
§ 371 (c)(1),
(2) Date: Mar. 22, 2018

(87) PCT Pub. No.: WO2017/049395
PCT Pub. Date: Mar. 30, 2017

(65) Prior Publication Data
US 2018/0263723 A1     Sep. 20, 2018

Related U.S. Application Data

(60) Provisional application No. 62/222,240, filed on Sep. 23, 2015.

(51) Int. Cl.
*A61B 90/50* (2016.01)
*H04N 5/232* (2006.01)
(Continued)

(52) U.S. Cl.
CPC ............. *A61B 90/37* (2016.02); *A61B 90/25* (2016.02); *A61B 90/35* (2016.02); *A61B 90/361* (2016.02);
(Continued)

(58) Field of Classification Search
CPC ..... A61B 1/05; A61B 90/361; H04N 5/23296
See application file for complete search history.

(56) References Cited

U.S. PATENT DOCUMENTS

| | | | |
|---|---|---|---|
| 6,899,442 B2* | 5/2005 | Howell | E04B 9/006 248/278.1 |
| 9,250,061 B2* | 2/2016 | Lorbeer | G01N 21/4795 |
| 9,492,089 B2* | 11/2016 | Hielscher | A61B 5/0053 |
| 2010/0078576 A1* | 4/2010 | Ntziachristos | A61B 5/0073 250/459.1 |
| 2015/0018622 A1* | 1/2015 | Tesar | A61B 1/05 600/202 |

(Continued)

FOREIGN PATENT DOCUMENTS

| | | |
|---|---|---|
| CN | 202631839 U | 12/2012 |
| CN | 203874032 U | 5/2014 |

(Continued)

*Primary Examiner* — Paulos M Natnael
(74) *Attorney, Agent, or Firm* — Norton Rose Fulbright Canada LLP; Reno Lessard

(57) ABSTRACT

The electronic vision system for assisting a skin care professional during treatment generally has: a support structure; a monitor being mounted to the support structure and having a sagittal plane; a video camera mounted to the support structure via an articulation, a field of view extending along an optical axis and a sagittal axis, the articulation having at least one pivot joint allowing pivoting movement of the optical axis relative to the monitor and preventing rotation of the video camera relative to the monitor and maintaining the parallelism of the sagittal axis of the video camera and the sagittal plane of the monitor; and a signal connection between the video camera and the monitor allowing the monitor to display a real-time video.

18 Claims, 9 Drawing Sheets

(51) Int. Cl.
*H04N 5/225* (2006.01)
*A61B 90/25* (2016.01)
*A61B 90/35* (2016.01)
*A61B 17/00* (2006.01)
*A61B 90/00* (2016.01)
*H04N 7/18* (2006.01)

(52) U.S. Cl.
CPC ........... *A61B 90/50* (2016.02); *H04N 5/2251* (2013.01); *H04N 5/2253* (2013.01); *H04N 5/23293* (2013.01); *H04N 7/183* (2013.01); *A61B 2017/00747* (2013.01); *A61B 2017/00752* (2013.01); *A61B 2017/00761* (2013.01); *A61B 2090/372* (2016.02); *H04N 5/2256* (2013.01); *H04N 5/23296* (2013.01)

(56) References Cited

U.S. PATENT DOCUMENTS

| | | | |
|---|---|---|---|
| 2015/0238073 A1* | 8/2015 | Charles | A61B 17/02 600/102 |
| 2015/0250387 A1 | 10/2015 | Hauger et al. | |
| 2015/0327765 A1* | 11/2015 | Crane | A61B 5/0059 348/77 |

FOREIGN PATENT DOCUMENTS

| | | |
|---|---|---|
| WO | 2012047773 A1 | 4/2012 |
| WO | 2013096850 A1 | 6/2013 |
| WO | 2015042460 A1 | 3/2015 |
| WO | 2015042460 A9 | 3/2015 |

* cited by examiner

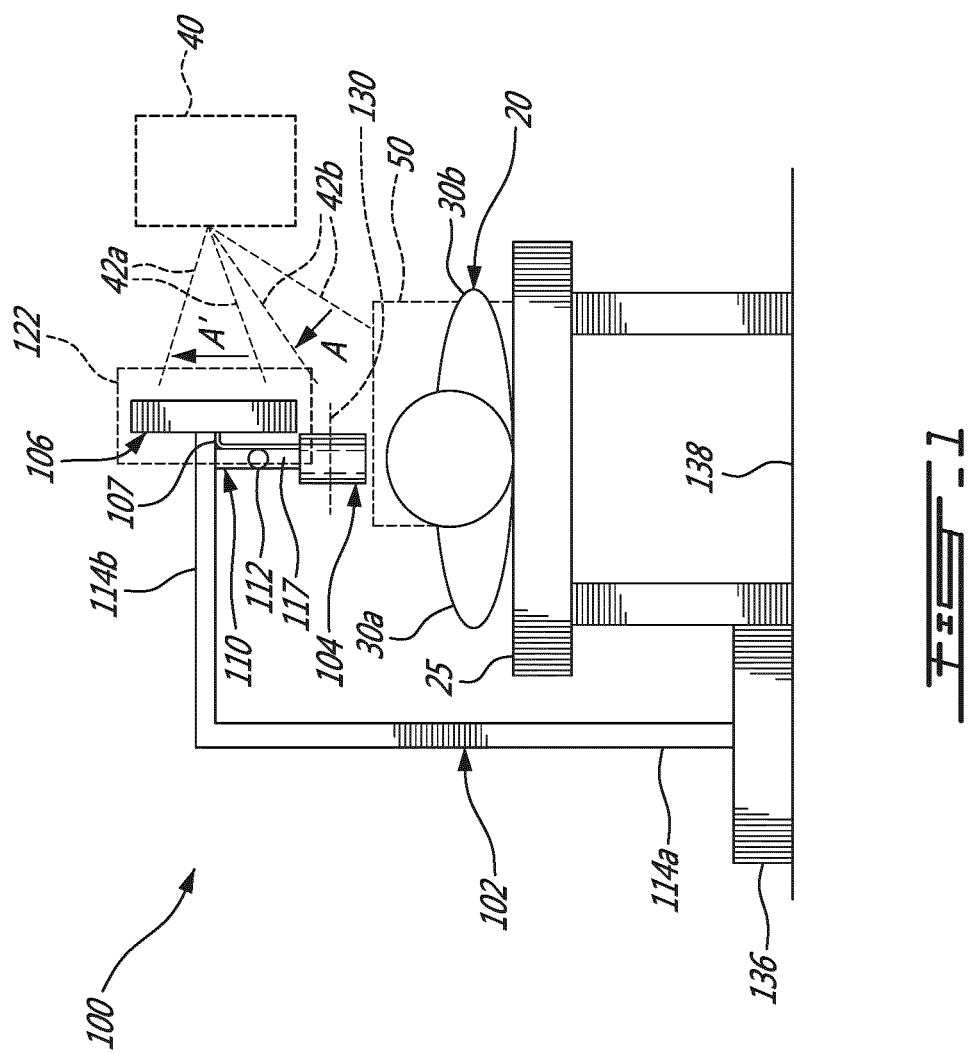

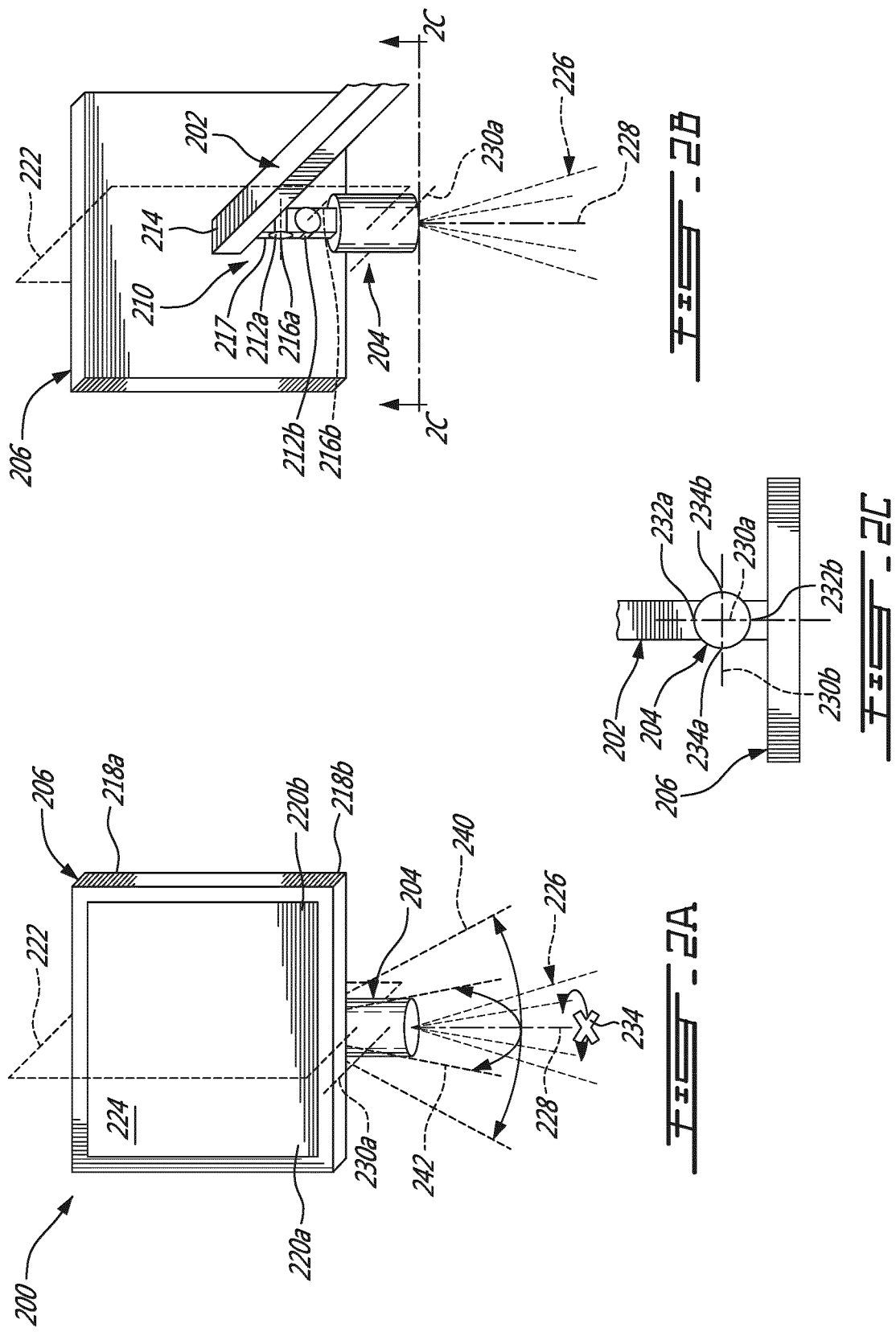

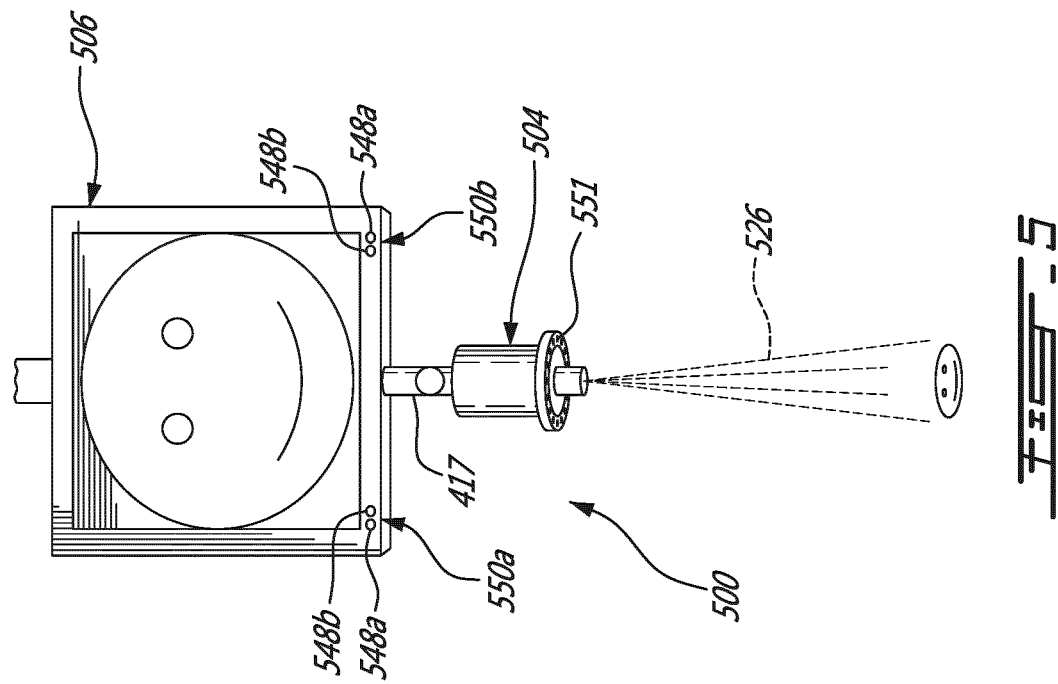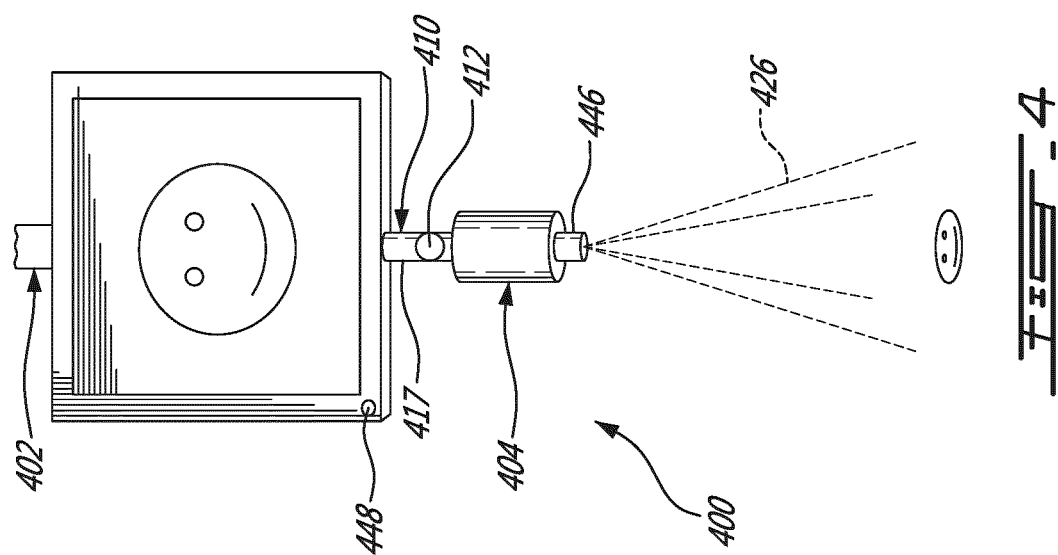

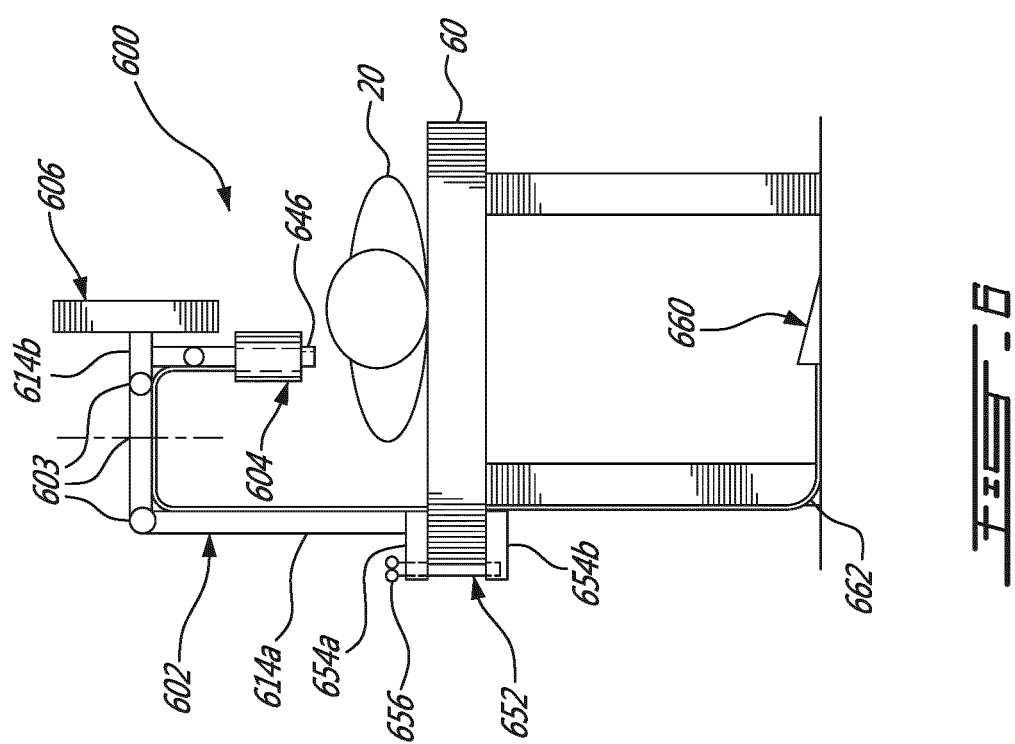

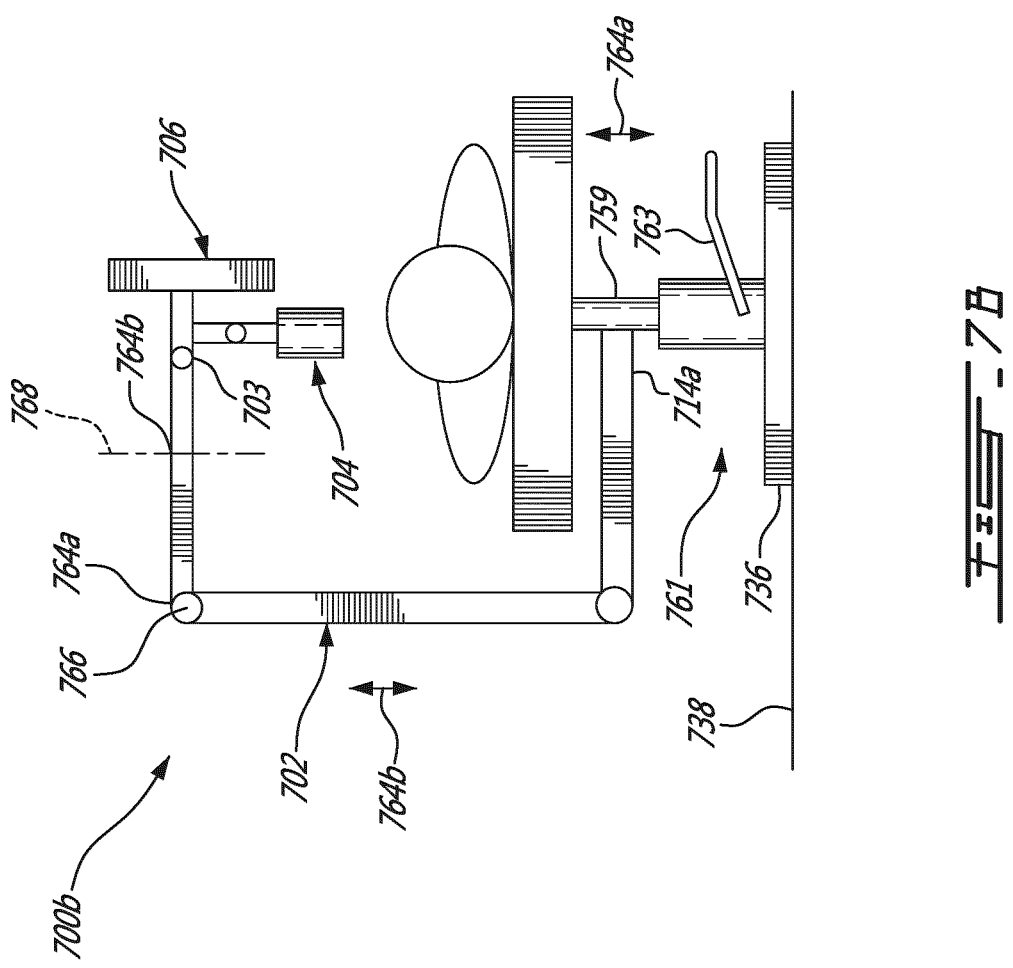

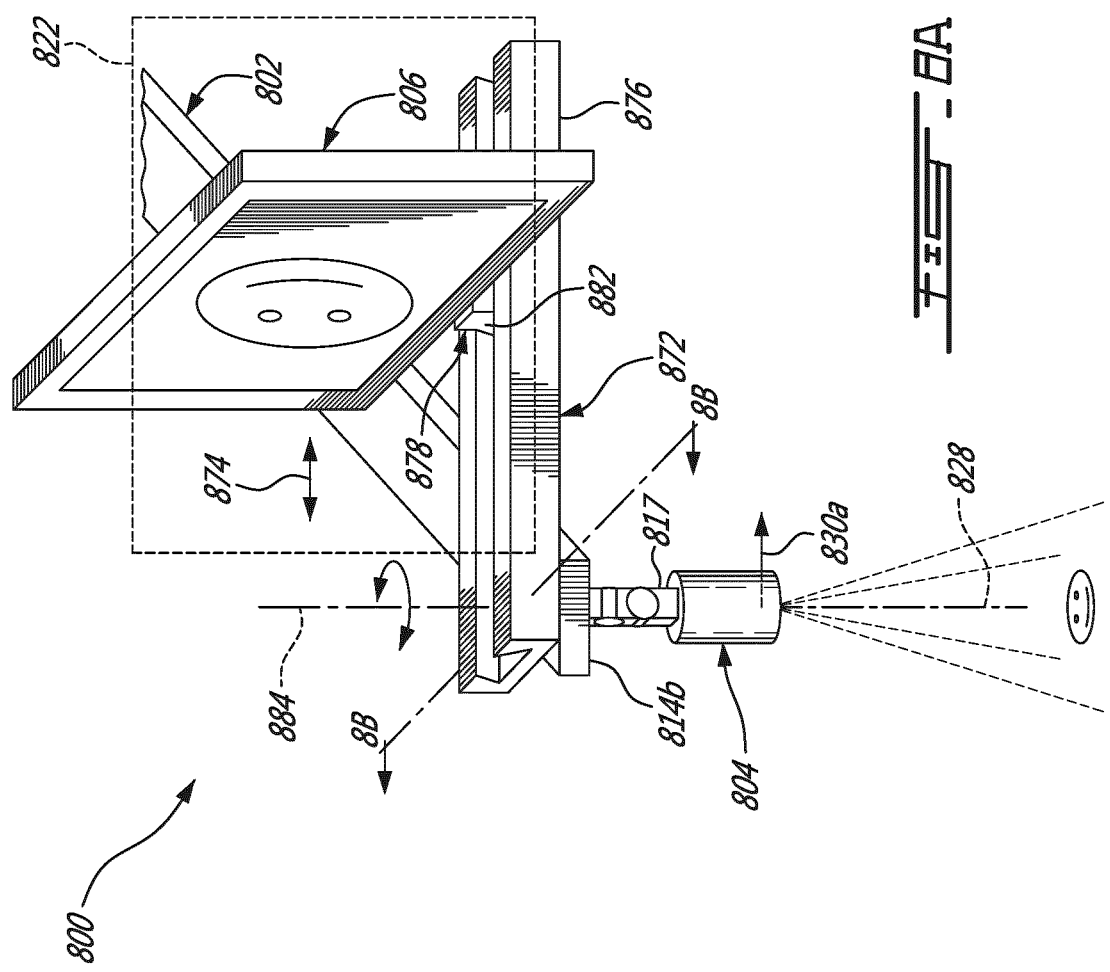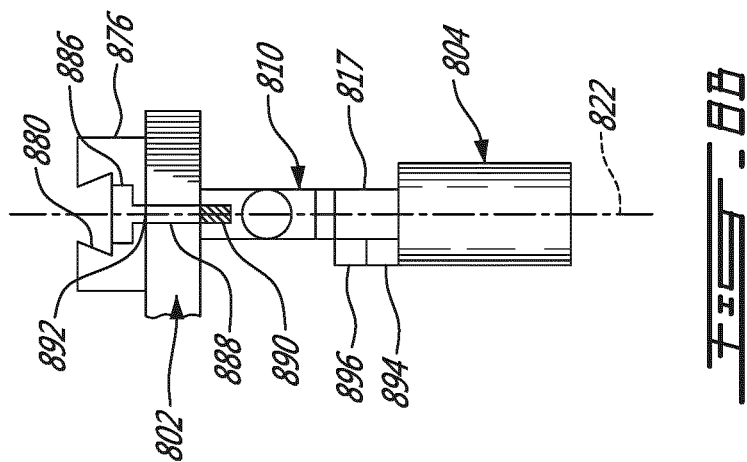

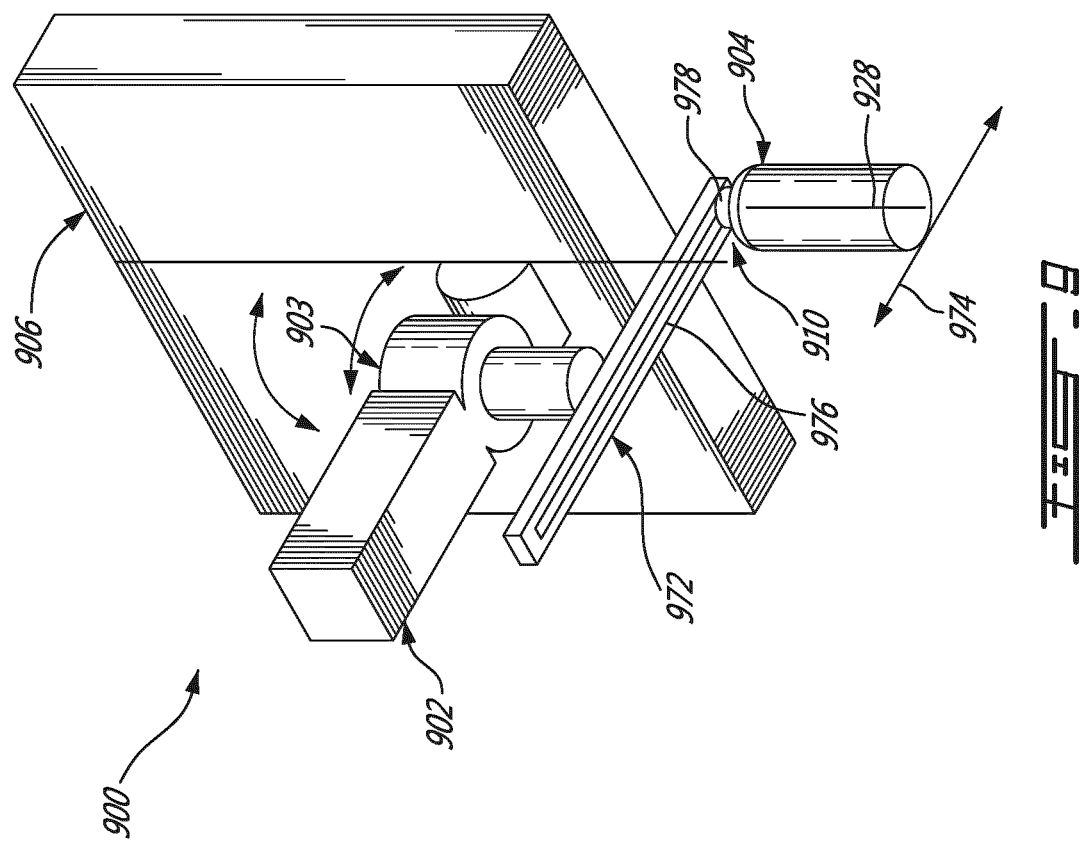

ELECTRONIC VISION SYSTEM AND USE THEREOF

FIELD

The improvements generally relate to systems and methods for assisting a skin care professional during treatment of the skin of a patient.

BACKGROUND

Skin care professionals such as estheticians, electrologists and therapists generally treat the skin (e.g. remove unwanted hair or lesion, treat skin imperfections) of their patients while sitting next to them such that the skin care professionals will typically look at the skin of their patients in a position of uncomfortable ergonomics, with or without a magnifying lamp. There thus remains room for improvement.

SUMMARY

There is provided an electronic vision system for assisting a skin care professional. The electronic vision system has a support structure, a monitor, a camera and a signal connection allowing the monitor to display a real-time video acquired by the camera. The camera is mounted to the support structure via an articulation which is configured to maintain a correspondence between the actual movement of the skin care professional and the imaged movement associated with the real-time video as displayed to the skin care professional by the monitor.

In accordance with an aspect, the monitor is mounted to the extremity of the support structure via an articulated member having axes such that the monitor can be panned towards either lateral side of the support structure and tilted up or down. The camera is mounted to the support structure via an articulation that has two pivot joints allowing pan (left and right movements) and tilt (front and back movements) while maintaining the image in the same axial plane as the monitor regardless of the placement of the camera with respect to the axis of the monitor. In a further embodiment, the camera and monitor can be displaced longitudinally from one another such that the skin care professional can place the camera closer or farther to themselves than the monitor.

In accordance with another aspect, there is provided an electronic vision system for assisting a skin care professional during treatment (e.g., epilation, treat skin imperfections, remove lesions) of a portion of the skin of a patient, the system comprising: a support structure; a monitor having a display screen and a sagittal plane and being mounted to the support structure; a video camera having a body mounted to the support structure via an articulation, a field of view extending along an optical axis and a sagittal axis, the articulation having at least one pivot joint allowing pivoting movement of the optical axis of the video camera relative to the monitor and preventing rotation of the video camera about the optical axis relative to the monitor and maintaining the parallelism of the sagittal axis of the video camera and the sagittal plane of the monitor; and a signal connection between the video camera and the monitor allowing the monitor to display a real-time video provided by the video camera. In this embodiment, the signal connection can allow the monitor to display the real-time video provided by the video camera wherein the portion of the field of view which is on the left side of the sagittal plane is displayed on the left side of the display screen and the portion of the field of view which is on the right side of the sagittal plane is displayed on the right side of the display screen. This way, the monitor can display the portion of the skin of the patient to the skin care professional during the treatment in a manner allowing to maintain a correspondence between the actual movement of the skin care professional and the imaged movement associated with the real-time video as displayed to the skin care professional on the monitor.

In accordance with another aspect, there is provided a use of an electronic vision system during a treatment of a portion of the skin of a patient by a skin care professional, the electronic vision system comprising: a support structure; a monitor having a display screen and being mounted to the support structure; a video camera having a body mounted to the support structure via an articulation; and a signal connection between the video camera and the monitor allowing the monitor to display a real-time video provided by the video camera showing the portion of the skin of the patient to the skin care professional during the treatment.

Many further features and combinations thereof concerning the present improvements will appear to those skilled in the art following a reading of the instant disclosure.

DESCRIPTION OF THE FIGURES

In the figures,

FIG. 1 is a side elevation view of an example of an electronic vision system for assisting a skin care professional, in accordance with an embodiment;

FIG. 2A is an oblique, front and partial view of an electronic vision system for assisting a skin care professional showing pan and tilt ranges, in accordance with an embodiment;

FIG. 2B is an oblique, back and partial view of the electronic vision system shown in FIG. 2A, in accordance with an embodiment;

FIG. 2C is a bottom plan and partial view of the electronic vision system taken along line 2C-2C of FIG. 2A, in accordance with an embodiment;

FIG. 4 is a partial perspective view of another example of an electronic vision system for assisting a skin care professional, showing a zoom and an exemplary actuator of the zoom, in accordance with an embodiment;

FIG. 5 is a partial perspective view of another example of an electronic vision system for assisting a skin care professional, showing a lighting element, in accordance with an embodiment;

FIG. 6 is a side elevation view of another example of an electronic vision system for assisting a skin care professional with a support structure secured to a tabletop, in accordance with an embodiment;

FIG. 7B is a side elevation view of another example of an electronic vision system for assisting a skin care professional with a support structure secured to an hydraulic pump assembly, in accordance with an embodiment;

FIG. 8A is a partial perspective view of another example of an electronic vision system for assisting a skin care professional, showing a monitor mounted to a rail assembly, in accordance with an embodiment;

FIG. 8B is a partial cross sectional view of the electronic vision system taken along line 8B-8B of FIG. 8A; and FIG. 9 is a partial perspective view of another example of an electronic vision system for assisting a skin care professional, showing a camera mounted to a rail assembly, in accordance with an embodiment.

DETAILED DESCRIPTION

Figure 3B:
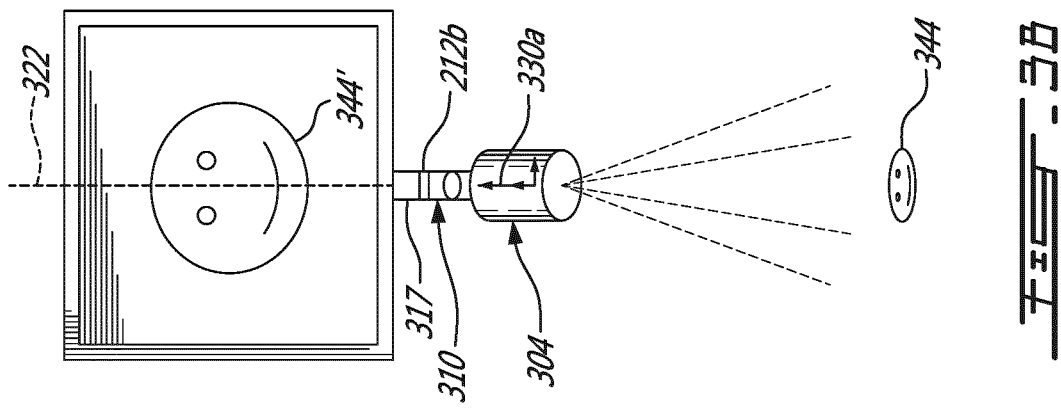
FIG. 3B is a front elevation view of another example of an electronic vision system for assisting a skin care professional, showing an example of a tilt movement, in accordance with an embodiment.

FIG. 1A shows a side elevation view of an example of an electronic vision system 100 for assisting a skin care professional for the treatment of the skin of a patient 20. This example shows the electronic vision system 100 in an exemplary environment in which the electronic vision system 100 can be used. For ease of understanding, the electronic vision system 100 is broadly described by collectively referring to FIG. 1 and to FIGS. 2A-C before describing each specific embodiment presented in this disclosure. Like elements bear like reference numerals.

As shown in FIG. 1, the electronic vision system 100 has a support structure 102, a video camera 104 and a monitor 106 configured to assist the skin care professional during treatment of the patient 20 while she/he is lying on a tabletop 25 or sitting in a treatment chair. As shown, the video camera 104 and the monitor 106 are mounted to the support structure 102 which maintains the video camera 104 and the monitor 106 into position during use. It is noted that the system 100 has a signal connection 107 between the video camera 104 and the monitor 106. The signal connection 107 is shown to be a wired signal connection. In another embodiment, the signal connection 107 is a wireless signal connection. The camera video can be any type of camera video capable of acquiring electronic moving images and generating a video signal in accordance with the electronic moving images. The monitor can be any type of monitor capable of displaying a real-time video based on the video signal. In an embodiment, the monitor 106 is a flat panel display. Such flat panel displays can be satisfactory for their lightness and small footprint. Any other suitable type of monitor can be used. For instance, any electronic device having a display screen such as a smart phone or an electronic table can be used.

In the example illustrated in FIG. 1, the support structure 102 is positioned adjacent to a lateral side 30a of the patient 20 while the skin care professional is positioned adjacent to the other lateral side 30b of the patient 20, and the video camera 104 is directed towards any portion of the skin (e.g. the body) of the patient 20 that is to be treated (referred to as "skin portion" hereinafter). During use, the video camera 104 provides the video signal to the monitor 106 using the signal connection 107 such that the monitor displays the real-time video based on the video signal. The real-time video is displayed on the monitor 106 and along a projection path of the monitor 106 in order to reach the eyes of the skin care professional, which can be positioned into a viewing space 40. In other words, the skin care professional, during treatment, can have sightlines 42a with the monitor 106 and sightlines 42b with a working space 50 in which lies the skin portion. The viewing space 40 shown in FIG. 1 is an example and should not be construed !imitatively. The real-time video can assist the skin care professional in providing satisfactory ergonomics during treatment of the skin portion. With such an electronic vision system 100, the skin care professional can avoid performing the treatment to the skin portion while being in a crooked position, which can be undesirable.

As shown, the video camera 104 is mounted to the support structure 102 via an articulation 110 which has one or more pivot joints (referred to as "pivot joint 112"). It is noted that the articulation 110 is generally directed downwardly while the monitor 106 is pivotable to display the real-time video towards a comfortably positioned skin care professional. In an embodiment, the projection path of the monitor 106 forms an acute, right or obtuse angle (e.g. 60°, 90°, 120°) with an optical axis of the camera 104. Accordingly, the pivot joint 112 assists the skin care professional to image the skin portion of the patient 20 while allowing the skin care professional to treat it ergonomically. For instance, FIG. 1 shows that the pivot joint 112 can allow a tilt movement of the video camera 104 relative to the monitor 106. In another embodiment, the pivot joint 112 can allow a translation movement of the video camera 104 as well as a pan movement of the video camera relative to the monitor 106. Such movements will be described in detail further below.

In an embodiment, the articulation 110 allows certain types of movement and prevents a given type of movement such that the skin care professional can see both the skin portion of the patient 20 along sightlines 42b, and the imaged skin portion along sightlines 42a. In this way, from the skin care professional's point of view, an orientation of the actual skin portion of the patient 20 and an orientation of the imaged skin portion correspond with one another. For instance, if the skin care professional makes an actual movement along direction A relative to the patient, the real-time video shows an imaged movement along direction A' which, as seen by the skin care professional on the monitor 106, appears parallel to the actual movement of the skin care professional. It was found that such correspondence between the actual movement and the imaged movement can help the skin care professional in satisfactorily and efficiently performing the treatment to the skin portion of the patient because it tends to reduce confusion between what movement is done by the skin care professional and what is seen on the monitor 106.

In order to maintain the correspondence between the actual movement of the skin care professional and the imaged movement as discussed above, the system 100 maintains the parallelism between a sagittal axis of the video camera 104 and a sagittal plane of the monitor 106 (these terms are further detailed with reference to FIGS. 2A-C). Indeed, FIG. 1 shows that the articulation 110 has a single pivot joint 112 allowing pivoting movement of the video camera 104 relative to the monitor 106 and a holding portion 117 preventing rotation of the video camera 104 about its optical axis and relative to the monitor 106.

FIGS. 2A-C show another example of an electronic vision system 200 for assisting a skin care professional. In this embodiment, a monitor 206 is fixedly mounted to an end 214 of a support structure 202, and a video camera 204 is mounted to the end 214 of the support structure 202 via an articulation 210. In the illustrated embodiment, the end 214 of the support structure 202 extends perpendicularly from the back of the monitor 206. The video camera 204 is connected to the monitor 206 via a signal connection which is wireless. In this illustrated embodiment, the articulation 210 is a combination of two pivot joints 212a,b having respective pivot axes 216a,b which are orthogonal to one another and which are both normal to an optical axis 228 of the video camera 204. The pivot joints 212a,b collectively allow the video camera 204 to be tilted and panned relative to the monitor 206.

For clarity and ease of understanding, it is understood that the monitor 206 has a sagittal plane 222 which divides a display screen 224 of the monitor 206 into two equal lateral regions. In other words, the sagittal plane 206 separates a left side 220a of the display screen from a right side 220b of the display screen and is normal to the display screen 224. It is also understood that the video camera 204 has a field of view 226 which extends from the video camera 204 along the optical axis 228 of the video camera 204. Referring now to FIGS. 2A-C, the video camera 204 has a sagittal axis 230a between top and bottom portions 232a,b of the video camera 204 and a lateral axis 230b between lateral portions 234a,b of the video camera 204, the sagittal axis 230a and the lateral axis 230b being both orthogonal to the optical axis 228. Using these definitions, it is understood that the pan movement of the video camera 204 occurs when the video camera 204 is pivoted about the sagittal axis 230a, and the tilt movement of the video camera 204 occurs when the video camera 204 is pivoted about the lateral axis 230b. In an embodiment, the pan movement has a pan range 240 between 0° and 45°, preferably between 0° and 90°, and most preferably between 0° and 180°. In another embodiment, the tilt movement has a tilt range 242 between 0° and 45°, preferably between 0° and 90°, and most preferably between 0° and 180°. It is understood that the articulation 110 can be moved with a relatively acceptable force and that the articulation 110 is sufficiently strong to maintain any given configuration after being moved.

In order to maintain the correspondence between the actual movement of the skin care professional and the imaged movement as discussed above, the articulation 210 has a holding portion 217 which prevents the video camera 204 to rotate about the optical axis 228 (i.e. roll movement is prevented, see reference numeral 234) and relative to the monitor 206. It is understood that the video camera 204 can be rotated about the optical axis 228 as long as the monitor 206 is rotated about the optical axis 228 together with the video camera 204. In other words, the articulation 210 allows the video camera 204 to rotate about the optical axis 228 together with the monitor 206 such that the correspondence between the actual movement of the skin care professional and the imaged movement can be maintained.

Figure 3A:
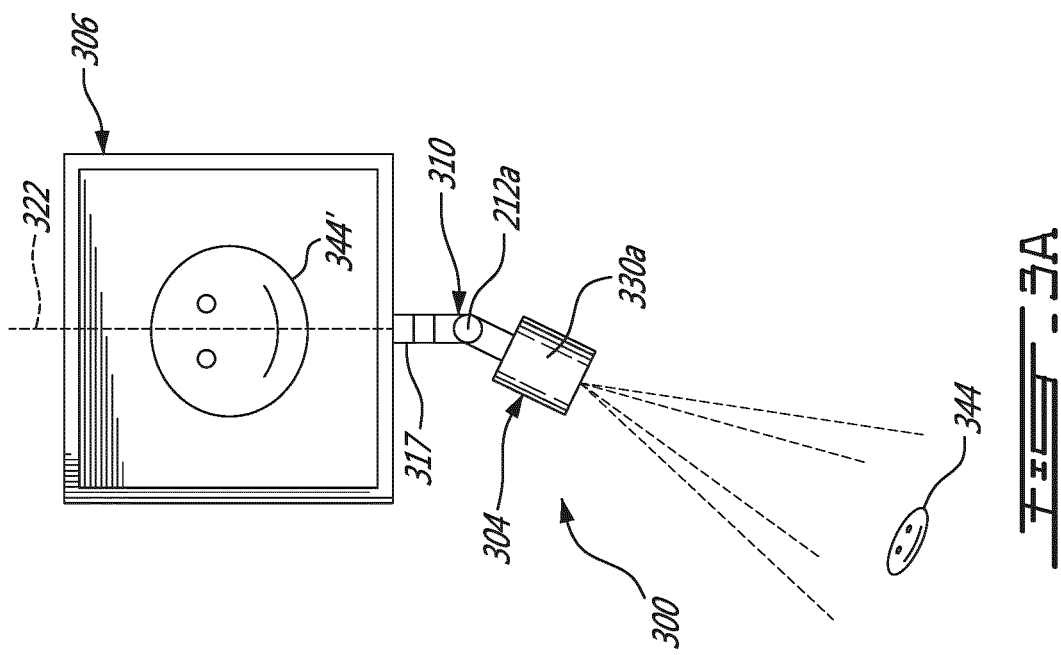
FIG. 3A is a front elevation view of another example of an electronic vision system for assisting a skin care professional showing an example of a pan movement, in accordance with an embodiment.

FIGS. 3A-B show front elevation views of an electronic vision system 300 for assisting a skin care professional, in accordance with an embodiment. Referring to FIG. 3A, the articulation 310 has a first pivot joint 312a which allows the video camera 304 to pan relative to the monitor 306. As shown, the holding portion 317 holds the sagittal axis of the video camera 330a (which is normal to the page in FIG. 3A) parallel to the sagittal plane 322 such that the skin portion, illustrated by exemplary directional pictogram 344, has an orientation which generally corresponds to an orientation of imaged directional pictogram 344'. Differently put, the top, bottom, left, and right portions of the directional pictogram 344 correspond to the top, bottom, left, and right imaged portions of the imaged directional pictogram 344' as seen by the skin care professional during use. Referring to FIG. 3B, the articulation 310 has second pivot joint 312b which allows the video camera 304 to tilt relative to the monitor 206. As illustrated, the sagittal axis 330a of the video camera 304 is parallel with the sagittal plane 322, which is indicating that the orientation of the directional pictogram 344 corresponds to the orientation of the imaged directional pictogram 344', which was found useful during treatment of the skin portion.

FIG. 4 shows another example of an electronic vision system 400 for assisting a skin care professional, in accordance with an embodiment. In this embodiment, the articulation 410 secures the video camera 404 indirectly to the support structure 402 via the monitor 406. As shown, the articulation 410 has a pivot joint 412 allowing a pan movement and a holding portion 417 preventing the video camera 404 to rotate about itself. As depicted, the video camera 404 has a camera lens with a zoom 446 that can be used to zoom in or zoom out. As will be understood by the skilled reader, some skin treatment can require a closer look to the skin portion, which can be provided by the zoom 446. In an embodiment, the zoom 446 can vary the magnification of the real-time video between 10× and 30×, or greater than 30×. The magnification can be obtained using an optical zoom, a numerical zoom or a combination thereof. In this embodiment, the electronic vision system 400 has an actuator 448 which can be used to actuate the magnification of the zoom 446. For instance, the actuator 448 can be provided in the form of a single rotatable button which can be turned clockwise in order to zoom in and which can be turned counterclockwise in order to zoom out. However, any other suitable type of zoom can be used. For instance, in alternate embodiments, the electronic vision system 400 can be provided with a kit of camera lenses wherein each camera lens has a different zooming factor. In these embodiments, the skin care professional can change a given camera lens for another camera lens depending on the magnification required for a given type of skin treatment to be performed.

FIG. 5 shows another example of an electronic vision system 500 for assisting a skin care professional, in accordance with an embodiment. As illustrated, the electronic vision system 500 has two pairs 550a,b of actuators 548a,b. Each of the pairs 550a,b of actuators 548a,b are provided in the form of push buttons where, for instance, the actuator 548a can be pushed to zoom in and the actuator 548b can be pushed to zoom out. It is understood that the pair 550a of actuators 548a,b, located to the left of the monitor 506 as seen by the skin care professional during use, can be convenient for right-handed skin care professionals while the other pair 550b of actuators 548a,b, located to the right of the monitor 506 as seen by the skin care professional during use, is likely to be more convenient for left-handed skin care professionals. However, it will be understood that the actuators can be provided at any suitable position of the monitor 506. It is understood that "zooming in" and "zooming out" vary the size of the field of view of the video camera. For instance, FIG. 4 shows a zoomed out field of view 426 compared with the zoomed in field of view 526 shown in FIG. 5.

The electronic vision system 500 can include a lighting element to light the portion of the skin of the patient while the skin is being imaged. As illustrated in this specific example, the lighting element is provided in the form of a lighting ring 551 positioned around the camera lens of the video camera 504 and directed in the same direction as the field of view 526, towards the skin of the patient. In this example, the lighting ring 551 includes a plurality of light-emitting diodes distributed around a circumference of the camera lens of the video camera 504. Any other suitable type of lighting ring, or lighting element can be used. It is noted that the color of the lighting provided by the lighting ring 551 can be chosen as a function of the color of the skin or hair of the patient and/or as a function of the type of skin perfections to image. For instance, in some embodiments, the lighting ring is adapted to provide a lighting beam in the red portion or near-infrared portion of the electromagnetic spectrum when capillaries are to be imaged. In some other embodiments, the lighting ring is adapted to provide a lighting beam in the white portion or the blue portion of the electromagnetic spectrum when dark spots of the skin are to be imaged. In alternative embodiments, the lighting ring is adapted to provide a lighting beam in the yellow portion of the electromagnetic spectrum when pale spots, scars or white hair of the skin are to be imaged. Other color may be used to image other type of objects.

Referring back to FIG. 1, the support structure 102 of the electronic vision system 100 is fixed from movement and provides the monitor 106 and the video camera 104 above the patient 20 during use. In this embodiment, the monitor 106 and the video camera 104 are fixedly mounted to the support structure 102. However, in another embodiment, the monitor 106 and the camera 104 are removably mounted to the support structure 102. As depicted, the support structure 102 has a first end 114a mounted to a base 136 and a second end 114b where the video camera 104 and the monitor 106 are mounted. In this embodiment, the base 136 is disposed directly on floor 138. The base 136 can be manually moved on the floor 138.

FIG. 6 shows another example of an electronic vision system 600 for assisting a skin care professional during treatment of the skin of the patient 20, in accordance with an embodiment. As depicted, the support structure 602 is mounted to a tabletop 60 or to an edge thereof. The support structure 602 has a first end 614a mounted directly to the tabletop 60 via a support clamp 652 that tightens two ends 654a,b of the support clamp 652 to the tabletop 60 via a wingnut 656, for instance. Any other type of support claim can also be used. Indeed, in another embodiment, the support structure 602 can be slidably mounted to the edge of the tabletop 60 for sliding movement therealong. The support structure 602 is provided in the form of an articulated arm having one or more articulated members 603 which can move the electronic vision system 600 by exerting a force on the electronic vision system 600. For instance, in the embodiment shown, the support structure 602 is pivotable in all directions such that the electronic vision system 600 can be rolled, tilted and panned during use. For clarity, the articulated members 603 allow the monitor 606 and the camera 604 to be collectively pivoted by the skin care professional. It is understood that the articulated arm can be moved with an acceptable force and that the articulated arm is sufficiently strong to maintain any given configuration after being moved. In this embodiment, the video camera has a zoom 646 which can be used to zoom in or zoom out the images of the real-time video relative to the portion of the skin of the patient 20 such as the one described above. In this embodiment, the zoom 646 is actuatable by a foot of the skin care professional via a pedal assembly 660 in communication with the zoom 646 via electrical cord 662. In this embodiment, the electrical cord 662 runs along the support structure 602 before reaching the camera 604.

Figure 7A:
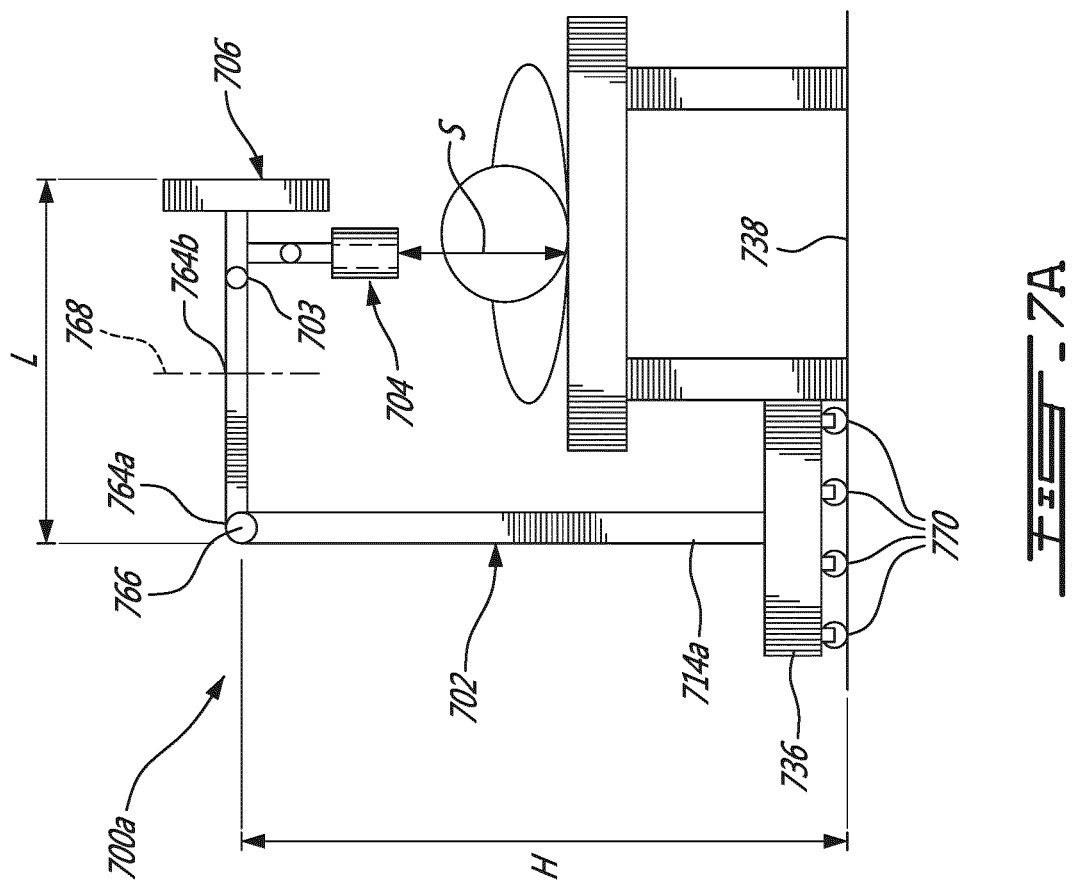
FIG. 7A is a side elevation view of another example of an electronic vision system for assisting a skin care professional with a support structure having a base with casters, in accordance with an embodiment.

FIG. 7A shows another example of an electronic vision system 700a for assisting a skin care professional, in accordance with an embodiment. In this embodiment, the support structure 702 is provided in the form of an articulated arm having first and second joints 764a,b. The first joint 764a has a horizontal axis of rotation 766 (through the page) which allows the monitor 706 and the video camera 704 to be tilted vertically relative to the skin care professional, and the second joint 764b has an upright axis 768 which allows the monitor 706 and the video camera 704 to be panned laterally relative to the skin care professional during use. Also shown in this embodiment is the articulated member 703 which can be used to roll, tilt and pan the electronic vision system 700a during use. In this embodiment, the support structure 702 has a first end 714a which is secured to a base 736. The base 736 has a plurality of casters 770 allowing the electronic vision system 700a to be displaced with ease on the floor 738. In an embodiment, the casters 770 can be provided in the form of caster balls.

As shown, the electronic vision system 700a is adapted to image any portion of the skin of the patient. More specifically, in this example, the first and second joints 764a and 764b, the articulated member 703 and the casters 770 collectively allow the skin care professional to move the video camera 704 and the monitor 706 anywhere over the patient as desired. In some embodiments, the articulated arm of the support structure 702 may have an extending portion having a length L greater than a width of the table. For instance, the length L can be at least 35 inches when the table has a width of 30 inches. In some embodiments, the articulated arm of the support structure 702 has a height H which provides a suitable spacing S between the video camera 704 and the top of the table. In these embodiments, the spacing can be adjusted to fit with any patient. In alternate embodiments, the support structure 702 is adapted to be collapsible such as to reduce its footprint when not in use. As a result, when it is desired to store the support structure 702, it can be collapsed and moved at a storage area, for instance.

FIG. 7B shows another example of an electronic vision system 700b for assisting a skin care professional, in accordance with an embodiment. As depicted, the electronic vision system 700b has the first end 714a secured to a lift cylinder 759 of an hydraulic pump assembly 761. The hydraulic pump assembly 761, typically provided as part of an hydraulic pump chair, has the base 736 which rests on the floor 738 for supporting the patient and the electronic vision system 700b. When actuated, e.g. by a foot of the skin care professional, foot actuator 763 can cause the hydraulic pump assembly 761 to move the lift cylinder 759 up or down along bidirectional arrow 764a thus causing the electronic vision system 700b to be lifted up or down correspondingly along bidirectional arrow 764b. By providing such an hydraulic pump assembly, the skin care professional can lift the patient as desired while maintaining a satisfactory distance between the patient and the camera 704 during use, for instance.

FIGS. 8A-B show another example of an electronic vision system 800 for assisting a skin care professional, in accordance with another embodiment. As shown in FIG. 8A, the monitor 806 is mounted to the support structure 802 via a rail assembly 872 which forms an angle (e.g. acute) relative to the support structure 802. The rail assembly 872 allows the monitor 806 to be slid back and forth from the skin care professional and along a longitudinal orientation 874 while keeping the camera 804 in a relatively steady position relative to the skin portion of the patient. By doing so, the skin care professional can set the monitor 806 at a comfortable viewing distance from his/her eyes. More specifically, the rail assembly 872 has a longitudinal guide rail 876 mounted to the support structure 802 and a slidable member 878 mounted to the monitor 806. As shown in this example, the longitudinal guide rail 876 has a cross section having a trapezoidal shape wherein the smaller side of the trapezoidal shape is open (see FIG. 8B). The slidable member 878 has a trapezoidal-shaped bottom member 882 which snugly corresponds to the shape of the groove 880. In use, the slidable member 878 is slidably engaged into the groove 880 of the longitudinal guide rail 876 which allows movement of the monitor 806 along the longitudinal orientation 874. In alternate embodiments, the monitor 806 can be slidable along the longitudinal orientation 874 using a telescopic assembly. Other suitable sliding assemblies can be used.

It is noted that, in this embodiment, the sliding assembly 872 is pivotably mounted to the end 814b of the support structure 802. More specifically, the sliding assembly 872 can be rotated about an azimuth 884 which is generally in the sagittal plane 822 of the monitor 806. In order to maintain the correspondence between the skin portion and the imaged skin portion, the electronic vision system 800 has a holding portion 817 which prevents rotation of the video camera 804 relative to the monitor 806 but allows rotation of the video camera 804 when the sliding assembly 872 is rotated about the azimuth 884. Referring to the embodiment shown in FIG. 8B, such correspondence is maintained by rotatably fixing an end of the sliding assembly 876 with the articulation 810. In this embodiment, the end of the sliding assembly 876 has a bolt receiving chamber 886 along the azimuth 884, the end 814b has a bore 888, and the articulation 810 has a threaded bore 890. When assembled, a bolt 892 is threadingly attached to the threaded bore 890 via the bore 888, which rotatably fixes the end of the sliding assembly 872 to the video camera 804.

Still referring to FIG. 8B, the electronic vision system 800 has a processing unit 894 in communication with the video camera 804 and a computer-readable memory 896, in accordance with an embodiment. In this illustrated example, the processing unit 894 is configured to store, on the computer-readable memory 896, a digital recording of the real-time video recorded during a given period of time. The recording of the real-time video can be initiated by a record button of the processing unit 894, for instance. Such digital recordings can be used in order to generate video tutorials associated with a given type of skin treatment. In an embodiment, a skin care tutor records a digital tutorial of a given skin treatment that he/she is performing on a patient such that the digital tutorial recording can be sold to other skin care professionals desirous of learning how to perform the given skin treatment to their own patients. Although the processing unit 894 and the computer-readable memory 896 are shown to be mounted to the video camera 804, it is understood that the processing unit 894 and the computer-readable memory 896 can be secured in a casing of the video camera 804. Alternately, the processing unit 894 and the computer-readable memory 896 can be secured to the monitor 804 or at any place deemed suitable by the person having skilled in the art.

FIG. 9 shows another example of an electronic vision system 900 for assisting a skin care professional, in accordance with another embodiment. The electronic vision system 900 has the support structure 902 to which is mounted the monitor 906 and the camera 904 via the articulated member 903. Similarly to the electronic vision system 800 described above, the electronic vision system 900 has a rail assembly 972. However, in this embodiment, the camera 904 is indirectly mounted to the support structure 902 via the rail assembly 972 such that the camera 904, instead of the monitor 906, can be longitudinally displaced along the longitudinal orientation 974. More specifically, the rail assembly 972 has the longitudinal guide rail 976 which is shaped to slidably engaged with the slidable member 978 mounted to the camera 904 for sliding the camera 904 therealong. During use, the articulated member 903 of the electronic vision system 900 allows the monitor 906 to be tilted and also allows the monitor 906, the rail assembly 972 and thus the camera 904 to be panned collectively. In accordance with the above, the camera 904 is mounted to the rail assembly 972 via the articulation 910 such that the camera 904 can be tilted and panned but not rotated about its optical axis 928.

As can be understood, the examples described above and illustrated are intended to be exemplary only. For instance, the holding portion can be provided in the form of a stopper preventing the video camera to rotate about its optical axis. The scope is indicated by the appended claims.

What is claimed is:

1. An electronic vision system for assisting a skin care professional during treatment of a portion of the skin of a patient, the electronic vision system comprising:
    an articulated arm having a first end being fixedly mountable to a surface, and a second end opposite the first end;
    a monitor mounted to the second end of the articulated arm, the monitor having a display screen and a sagittal plane;
    a video camera having a body mounted to the second end of the articulated arm via an articulation, the articulated arm allowing the monitor and the video camera to be moved together, a field of view extending along an optical axis and a sagittal axis, the articulation having at least one pivot joint allowing pivoting movement of the optical axis of the video camera relative to the monitor and preventing rotation of the video camera about the optical axis relative to the monitor in a manner maintaining the parallelism of the sagittal axis of the video camera and the sagittal plane of the monitor; and
    a signal connection between the video camera and the monitor allowing the monitor to display a real-time video provided by the video camera.

2. The electronic vision system of claim 1, wherein the sagittal plane of the monitor defining a left side of the display screen and a right side of the display screen, the monitor displaying the portion of the field of view being on the left side of the sagittal plane on the left side of the display screen and displaying the portion of the field of view being on the right side of the sagittal plane on the right side of the display screen for showing the portion of the skin of the patient to the skin care professional during the treatment.

3. The electronic vision system of claim 1, wherein the at least two pivot joints include two pivot joints orthogonal to one another and normal to the optical axis.

4. The electronic vision system of claim 3, wherein a first one of the pivot axes of the at least two pivot joints is normal to the sagittal plane of the monitor and a second one of the pivot axes is normal to a coronal plane of the monitor.

5. The electronic vision system of claim 1, wherein the articulation includes a holding portion for preventing rotation of the video camera about the optical axis of the video camera.

6. The electronic vision system of claim 1, wherein the video camera has a camera lens.

7. The electronic vision system of claim 6, wherein the camera lens is a zoom.

8. The electronic vision system of claim 7, wherein the zoom allows the video camera to vary the magnification of the video camera between 10x and 30x.

9. The electronic vision system of claim 7, further comprising at least one actuator in communication with the zoom for tuning the magnification of the zoom during use.

10. The electronic vision system of claim 9, wherein the at least one actuator is secured to the monitor and accessible by the skin care professional during use.

11. The electronic vision system of claim 9, wherein the at least one actuator is a pedal actuatable by a foot of the skin care professional.

12. The electronic vision system of claim 1, wherein the video camera is indirectly secured to the second end of the articulated arm via the monitor.

13. The electronic vision system of claim 1, wherein at least one of the camera and the monitor is secured to the second end of the articulated arm via a rail assembly having a longitudinal guide rail secured to the second end of the articulated arm and a slidable member secured to the at least one of the camera and the monitor, the slidable member engaging into the guide rail for sliding the at least one of the camera and the monitor therealong.

14. The electronic vision system of claim 1, wherein the surface is provided in the form of a tabletop.

15. The electronic vision system of claim 1, wherein the surface is provided in the form of a base having a plurality of casters.

16. The electronic vision system of claim 1, wherein the video camera has a resolution having at least 480 horizontal lines.

17. The electronic vision system of claim 1, further comprising a processing unit in communication with a computer-readable memory and with the video camera, the processing unit being configured for storing on the computer-readable memory a digital recording of the real-time video during a period of time.

18. The electronic vision system of claim 1, wherein the video camera includes a lighting element for lighting at least the field of view of the video camera.

* * * * *